United States Patent
Beadle et al.

(10) Patent No.: US 7,148,388 B2
(45) Date of Patent: Dec. 12, 2006

(54) PROCESS FOR PREPARING AND OLEFINIC HYDROCARBON MIXTURE

(75) Inventors: Stephen W. Beadle, Prairieville, LA (US); Cesar M. Cheng-Guajardo, Baton Rouge, LA (US); Carolyn B. Duncan, Baton Rouge, LA (US); David Wayne Turner, Raymond, ME (US); Ramzi Y. Saleh, Baton Rouge, LA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 10/508,982

(22) PCT Filed: Mar. 28, 2003

(86) PCT No.: PCT/US03/09520

§ 371 (c)(1),
(2), (4) Date: Sep. 24, 2004

(87) PCT Pub. No.: WO03/082779

PCT Pub. Date: Oct. 9, 2003

(65) Prior Publication Data

US 2005/0176991 A1     Aug. 11, 2005

Related U.S. Application Data

(60) Provisional application No. 60/368,874, filed on Mar. 29, 2002.

(51) Int. Cl.
C07C 2/66    (2006.01)
C07C 2/68    (2006.01)
C07C 2/70    (2006.01)
C07C 29/16   (2006.01)
C07C 309/31  (2006.01)

(52) U.S. Cl. .......................... 568/909; 562/87; 562/93; 562/94; 562/95; 585/7; 585/455; 585/459; 585/462; 585/463; 585/464; 585/465; 585/467; 585/533

(58) Field of Classification Search .................. 585/7, 585/455, 467, 533, 459, 462, 463, 464, 465; 562/87, 93, 95, 94; 568/909
See application file for complete search history.

(56) References Cited

U.S. PATENT DOCUMENTS

| | | | |
|---|---|---|---|
| 3,231,621 A | 1/1966 | Slaugh | 260/604 |
| 3,239,566 A | 3/1966 | Slaugh et al. | 260/604 |
| 3,239,569 A | 3/1966 | Slaugh et al. | 260/632 |
| 3,239,570 A | 3/1966 | Slaugh et al. | 260/632 |
| 3,239,571 A | 3/1966 | Slaugh et al. | 260/632 |
| 3,420,898 A | 1/1969 | Van Winkle et al. | 260/632 |
| 3,440,291 A | 4/1969 | Van Winkle et al. | 260/632 |
| 3,448,157 A | 6/1969 | Slaugh et al. | 260/604 |
| 3,448,158 A | 6/1969 | Slaugh et al. | 260/604 |
| 3,496,203 A | 2/1970 | Morris et al. | 260/439 |
| 3,496,204 A | 2/1970 | Morris et al. | 260/439 |
| 3,501,515 A | 3/1970 | Van Winkle et al. | 260/439 |
| 3,527,818 A | 9/1970 | Mason et al. | 260/632 |
| 3,960,978 A | 6/1976 | Givens et al. | 260/683.15 |
| 4,076,842 A | 2/1978 | Plank et al. | 423/328 |
| 4,150,062 A | 4/1979 | Garwood et al. | 260/673 |
| 4,211,640 A | 7/1980 | Garwood et al. | 208/255 |
| 4,227,992 A | 10/1980 | Garwood et al. | 208/46 |
| 4,298,547 A | 11/1981 | Young | 260/505 |
| 4,439,409 A | 3/1984 | Puppe et al. | 423/328 |
| 4,547,613 A | 10/1985 | Garwood et al. | 585/533 |
| 4,826,667 A | 5/1989 | Zones et al. | 423/277 |
| 4,855,527 A | 8/1989 | Page et al. | 585/527 |
| 4,954,325 A | 9/1990 | Rubin et al. | 423/328 |
| 5,026,933 A | 6/1991 | Blain et al. | 585/7 |
| 5,236,575 A | 8/1993 | Bennett et al. | 208/46 |
| 5,250,277 A | 10/1993 | Kresge et al. | 423/329.1 |
| 5,362,697 A | 11/1994 | Fung et al. | 502/71 |
| 6,077,498 A | 6/2000 | Diaz Cabanas et al. | 423/702 |

FOREIGN PATENT DOCUMENTS

EP    0293032       5/1988
WO    WO 97/17290   5/1997

OTHER PUBLICATIONS

Industrial Chemicals, Third Edition, pp. 60-62, W.L. Faith et al., John Wiley & Sons, Inc., (1965).

*Primary Examiner*—Peter G. O'Sullivan
(74) *Attorney, Agent, or Firm*—Andrew B. Griffis

(57) ABSTRACT

In a process for preparing an olefinic hydrocarbon mixture comprising at least 5% by weight of mono-olefin oligomers of the empirical formula:

$$C_nH_{2n}$$

where n is greater than or equal to 6, a feedstock comprising n-butene and propylene in a molar ratio of about 1:0.01 to about 1:0.49 is contacted under oligomerization conditions with surface deactivated ZSM-23. The resultant mono-olefin oligomers comprise at least 20 percent by weight of olefins having at least 12 carbon atoms, wherein said olefins having at least 12 carbon atoms have an average of from about 0.8 to about 2.0 $C_1$–$C_3$ alkyl branches per carbon chain.

3 Claims, No Drawings

PROCESS FOR PREPARING AND OLEFINIC HYDROCARBON MIXTURE

CROSS REFERENCE TO RELATED APPLICATIONS

This application is a National Stage Application of International Application No. PCT/US03/09520, filed Mar. 28, 2003, which claims the benefit of Provisional Application No. 60/368,874, filed Mar. 29, 2002. These applications are incorporated herein by reference.

FIELD

This invention relates to a process for preparing an olefinic hydrocarbon mixture.

BACKGROUND

Long chain olefins ($C_{10}+$) are important starting materials in the production of sulfonate surfactants, in which the olefins are used to alkylate aromatic hydrocarbons and the resultant alkyl aromatics are sulfonated to produce alkylaryl sulfonates. In addition, the alcohols of long chain olefins have considerable commercial importance in a variety of applications, including detergents, soaps, surfactants, and freeze point depressants in lubricating oils. In such applications, the degree and the position of the branching along the carbon chain of the olefin is often critical to the properties of the end product. Thus, for example, highly branched olefins tend to produce surfactants with poor biodegradability, whereas substantially linear olefins tend to produce surfactants with poor hard and cold water cleaning properties. In addition, it is found that lightly branched olefins, where the branching is at the odd-numbered positions in the carbon chain, produce surfactants with enhanced biodegradability as compared to similar olefins where the branching is at the even-numbered positions in the carbon chain.

One potential route for the production of long chain olefins is by the oligomerization of lower ($C_2$ to $C_6$) olefins, typically using an acidic catalyst, such as a zeolite. Thus, for example, it is known from U.S. Pat. Nos. 3,960,978, 4,150,062; 4,211,640; 4,227,992; and 4,547,613 to oligomerize lower olefins over ZSM-5, but the resultant oligomers are essentially linear.

U.S. Pat. No. 5,026,933 describes a process for producing high molecular weight, slightly branched hydrocarbon oligomers from a lower olefin feedstock employing a shape selective crystalline silicate catalyst, ZSM-23, which has been surface deactivated. The resultant oligomer mixture comprises at least 20% by weight of olefins having at least 12 carbon atoms and said olefins having at least 12 carbon atoms have an average of from 0.8 to 2.0 methyl branches per carbon chain. The lower olefin feedstock employed is either propylene or n-butene.

Further investigation of the process described in the '933 patent has now shown that, whereas oligomerization of n-butene produces oligomers in which the majority of the branching appears to be at the odd-numbered positions, such as the 3- and 5-positions, in the carbon chain, oligomerization of propylene produces oligomers in which the majority of the branching appears to be at the even-numbered positions in the carbon chain. Surprisingly, it has also been found that oligomerization of mixtures of n-butene and propylene at molar ratios up to 1:0.49 produces oligomers in which the position of the branching appears to be similar to that obtained with butene alone, i.e., apparently concentrated at the odd-numbered positions in the carbon chain. Since propylene is available in large quantities in a modern integrated oil refinery, this discovery provides an important extension to the applicability of the process of the '933 patent.

SUMMARY

Accordingly, the invention resides in a first aspect in a process for preparing an olefinic hydrocarbon mixture comprising at least 5 wt %, such as at least 20 wt %, for example at least 85 wt %, of mono-olefin oligomers of the empirical formula:

$$C_nH_{2n}$$

where n is greater than or equal to 6, said mono-olefin oligomers comprising at least 20 percent by weight of olefins having at least 12 carbon atoms, said olefins having at least 12 carbon atoms having an average of from about 0.8 to about 2.0 $C_1$–$C_3$ alkyl branches per carbon chain, said process comprising contacting a feedstock comprising n-butene and propylene in a molar ratio of about 1:0.01 to about 1:0.49, under oligomerization conditions with surface deactivated ZSM-23.

Conveniently, said feedstock contains n-butene and propylene in a molar ratio of about 1:0.05 to about 1:0.35.

Conveniently, the ZSM-23 has been surface deactivated with a sterically hindered nitrogenous base, such as 2,4,6-collidine.

In a second aspect, the invention resides in a process for producing a long chain alcohol mixture comprising contacting at least part of said olefinic hydrocarbon mixture with carbon monoxide and hydrogen under hydroformylation conditions and in the presence of a hydroformylation catalyst.

In a third aspect, the invention resides in a process for producing an alkylaromatic compound comprising contacting an aromatic compound with at least part of said olefinic hydrocarbon mixture under alkylation conditions and in the presence of an alkylation catalyst.

In yet a fourth aspect, the invention resides in a process for preparing an alkylaryl sulfonate by sulfonating the alkylaromatic compound produced in accordance with said third aspect of the invention.

DETAILED DESCRIPTION OF THE EMBODIMENTS

The present invention provides an improved process for producing slightly branched, high molecular weight olefinic hydrocarbons by oligomerizing a lower olefinic hydrocarbon feedstock in the presence of a surface-deactivated ZSM-23 catalyst. The use of such a catalyst allows the use of an olefin feedstock comprising a mixture of n-butene and propylene apparently without significant reduction in the amount of branching at the odd-numbered positions in the carbon chain of the resultant oligomers.

The hydrocarbon feedstock used in the process of the invention comprises n-butene and propylene in a molar ratio of n-butene to propylene of about 1:0.01 to about 1:0.49 and such as about 1:0.05 to about 1:0.35. In addition, the feedstock can contain low molecular weight, typically $C_4$–$C_6$, saturated hydrocarbons, which can act as a heat sink during the exothermic oligomerization process. In general, the feedstock can contain up to 80 wt %, or more typically up to 50 wt %, of paraffins.

The oligomerization catalyst used in the process of the invention comprises ZSM-23 which has been surface deactivated, conveniently by treatment with a sterically hindered nitrogenous base, such as a trialkyl pyridine compound, and preferably with 2,4,6-collidine (2,4,6-trimethyl pyridine, gamma-collidine). The surface deactivating compound should have a minimum cross-sectional diameter greater than the effective pore size of the zeolite to be treated; i.e., greater than 5 Angstroms. ZSM-23 and its characteristic X-ray diffraction pattern are described in detail in U.S. Pat. No. 4,076,842, the entire contents of which are incorporated herein by reference. In one embodiment, the ZSM-23 employed in the catalyst has an alpha value of about 25 and a crystal size of less than 0.1 micron and is conveniently composited with a binder, such as alumina.

Suitable oligomerization conditions include a temperature of about 160° C. to about 250° C., such as about 190° C. to about 230° C., for example about 210° C. to about 220° C.; a pressure in the range of about 500 psig (3447 kPa (gauge)) to about 1500 psig (10342 kPa (gauge)), such as in the range of about 750 psig (5171 kPa (gauge)) to about 1250 psig (8618 kPa (gauge)), and a feed weight hourly space velocity (WHSV) in the range of about 0.1 hr$^{-1}$ to about 4.0 hr$^{-1}$, such as in the range of about 0.2 hr$^{-1}$ to about 3.0 hr$^{-1}$, for example in the range of about 1.75 hr$^{-1}$ to about 2.25 hr$^{-1}$.

Where surface deactivation is achieved by treatment with a trialkyl pyridine compound, the feed to the oligomerization process includes additional trialkyl pyridine compound so that the surface properties of the zeolite are maintained during the process. Further details of the oligomerization process can be found in U.S. Pat. No. 5,026,933, the entire contents of which are incorporated herein by reference.

The product of the oligomerization process of the invention is an olefinic hydrocarbon mixture which comprises at least 5 wt %, such as at least 20 wt %, for example at least 85 wt %, of mono-olefin oligomers of the empirical formula:

$$C_nH_{2n}$$

wherein n is greater than or equal to 6 and wherein said mono-olefin oligomers comprise at least 20 wt %, such as at least 60 wt %, of olefins having at least 12 carbon atoms and said olefins having at least 12 carbon atoms have an average of from about 0.8 to about 2.0, such as about 0.8 to about 1.3, $C_1$–$C_3$ alkyl branches per carbon chain. Conveniently, the olefins having at least 12 carbon atoms contain no branches other than methyl groups and ethyl groups.

Despite the presence of propylene in the oligomerization feed, it is believed that at least 50% of the $C_1$–$C_3$ alkyl branches in the $C_{12}$+ olefinic product of the present process are located at the odd-numbered positions in the carbon chain.

By fractionating the olefinic hydrocarbon mixture produced by the oligomerization process of the invention it is possible to produce one or more olefinic fractions, for example a $C_{12}$ olefinic fraction comprising at least 85% by weight of mono-olefins having 12 carbon atoms, said mono-olefins having a straight backbone chain of at least 10 carbon atoms and an average of from about 0.8 to about 2.0 (such as about 0.8 to about 1.3) $C_1$–$C_3$ alkyl branches per carbon chain.

Part or all of the olefinic hydrocarbon mixture produced by the oligomerization process of the invention is conveniently used in the production of long chain alcohols for application as, for example, detergents, soaps, surfactants, and freeze point depressants in lubricating oils. Typically this is achieved by hydroformylation, that is, reaction with carbon monoxide and hydrogen, according to the Oxo process. Catalysts employed can be cobalt or rhodium which may be modified with phosphine, phosphite, arsine or pyridine ligands, as described in U.S. Pat. Nos. 3,231,621; 3,239,566; 3,239,569; 3,239,570; 3,239,571; 3,420,898; 3,440,291; 3,448,158; 3,448,157; 3,496,203; and 3,496,204; 3,501,515; and 3,527,818, the disclosures of which are incorporated herein by reference.

Typical hydroformylation reaction conditions include a temperature of about 125° C. to about 200° C., a pressure of about 2170 kPa to about 32550 kPa (300 psig to about 4000 psig) and a catalyst to olefin ratio of about 1:5000 to about 1:1. The molar ratio of hydrogen to carbon monoxide is usually about 0.5 to about 10, such as about 1 to about 2. The hydroformylation reaction typically produces an aldehyde which can then be hydrogenated to generate the required alcohol product.

The hydroformylation process can be carried out in the presence of an inert solvent, such as a ketone, e.g., acetone, methyl ethyl ketone, methyl isobutyl ketone, acetophenone and cyclohexanone; an aromatic compound, e.g., benzene, toluene and the xylenes; a halogenated aromatic compound, e.g., chlorobenzene and orthodichlorobenzene; a halogenated paraffinic hydrocarbon, e.g., methylene chloride and carbon tetrachloride; a paraffin, e.g., hexane, heptane, methylcyclohexane and isooctane and a nitrile, e.g., such as benzonitrile and acetonitrile.

The catalyst ligand may be made of tertiary organo phosphines, such as trialkyl phosphines, triamyl phosphine, trihexyl phosphine, dimethyl ethyl phosphine, diamylethyl phosphine, tricyclopentyl (or hexyl) phosphine, diphenyl butyl phosphine, dipenyl benzyl phosphine, triethoxy phosphine, butyl diethyoxy phosphine, triphenyl phosphine, dimethyl phenyl phosphine, methyl diphenyl phosphine, dimethyl propyl phosphine, the tritolyl phosphines and the corresponding arsines and stibines. Included as bidentate-type ligands are tetramethyl diphosphinoethane, tetramethyl diphosphinopropane, tetraethyl diphosphinoethane, tetrabutyl diphosphinoethane, dimethyl diethyl diphosphinoethane, tetraphenyl diphosphinoethane, tetraperfluorophenyl diphosphinoethane, tetraphenyl diphosphinopropane, tetraphenyl diphosphinobutane, dimethyl diphenyl diphosphinoethane, diethyl diphenyl diphosphinopropane and tetratrolyl diphosphinoethane.

Examples of other suitable ligands are the phosphabicyclohydrocarbons, such as 9-hydrocarbyl-9-phosphabicyclononane in which the smallest P-containing ring contains at least 5 carbon atoms. Some examples include 9-aryl-9-phosphabicyclo[4.2.1]nonane, (di)alkyl-9-aryl-9-phosphabicyclo[4.2.1]nonane, 9-alkyl-9-phosphabicyclo[4.2.1]nonane, 9-cycloalkyl-9-phosphabicyclo[4.2.1]nonane, 9-cycloalkenyl-9-phosphabicyclo[4.2.1]nonane, and their [3.3.1] and [3.2.1] counterparts, as well as their triene counterparts.

Alternatively, part or all of the olefinic hydrocarbon mixture produced by the oligomerization process of the invention can be used, either alone or in admixture with linear alpha-olefins, as an alkylating agent in a process for the selective alkylation of an aromatic compound (e.g., benzene) with a relatively long chain length alkylating agent to produce substantially linear phenylalkanes. The alkylation process is conducted such that the organic reactants, i.e., the aromatic compound and the olefinic hydrocarbon mixture, are contacted under effective alkylation conditions with a suitable acid catalyst. Suitable aromatic hydrocarbons include benzene, toluene, xylene and naphthalene, with preferred compounds being benzene and toluene.

In one embodiment, the catalyst is a homogeneous acid catalyst such as a Lewis acid catalyst, for example aluminum chloride. Alternatively, the homogeneous acid catalyst is a Brønsted acid catalyst, such as HF or phosphoric acid. Suitable alkylation conditions with a homogeneous catalyst include a temperature of from about −10° C. to about 100° C., a pressure of from about 100 kPa to about 2500 kPa (1.0 to 25 atmospheres), a feed weight hourly space velocity (WHSV) of from about 0.2 hr$^{-1}$ to about 10 hr$^{-1}$ and an aromatic compound to olefinic hydrocarbon mixture mole ratio of from about 1:1 to about 15:1. Typical reaction conditions include a temperature of from about 0° C. to about 50° C., a pressure of from about 100 kPa to about 300 kPa (1.0 to about 3.0 atmospheres), a feed weight hourly space velocity (WHSV) of from about 0.1 hr$^{-1}$ to about 0.5 hr$^{-1}$ and an aromatic compound to olefinic hydrocarbon mixture mole ratio of from about 5:1 to about 10:1. The reactants can be in either the vapor phase or the liquid phase and can be neat, i.e., free from intentional admixture or dilution with other material, or they can be brought into contact with the catalyst composition with the aid of carrier gases or diluents such as, for example, hydrogen or nitrogen.

In a further embodiment, the alkylation process is conducted in the presence of a heterogeneous catalyst, such as a molecular sieve. Suitable molecular sieves include mordenite, particularly dealuminized mordenite and other 6–7 Angstrom pore molecular sieves disclosed in U.S. Pat. No. 5,026,933, the entire contents of which are incorporated herein by reference.

In one practical embodiment, the alkylation catalyst comprises a molecular sieve having an X-ray diffraction pattern including d-spacing maxima at 12.4±0.25, 6.9±0.15, 3.57±0.07 and 3.42±0.07 Angstrom. The X-ray diffraction data used to characterize said molecular sieve are obtained by standard techniques using the K-alpha doublet of copper as the incident radiation and a diffractometer equipped with a scintillation counter and associated computer as the collection system. Materials having the required X-ray diffraction lines are sometimes referred to as molecular sieves of the MCM-22 family and include MCM-22 (described in U.S. Pat. No. 4,954,325), PSH-3 (described in U.S. Pat. No. 4,439,409), SSZ-25 (described in U.S. Pat. No. 4,826,667), ERB-1 is described in European Patent No. 0293032, ITQ-1 is described in U.S. Pat. No. 6,077,498, ITQ-2 is described in International Patent Publication No. WO97/17290, MCM-36 (described in U.S. Pat. No. 5,250,277), MCM-49 (described in U.S. Pat. No. 5,236,575) and MCM-56 (described in U.S. Pat. No. 5,362,697). The entire contents of said patents are incorporated herein by reference.

The molecular sieve alkylation catalyst can be combined in conventional manner with an oxide binder, such as alumina, such that the final alkylation catalyst contains between about 2 and about 80 wt % sieve.

With a molecular sieve catalyst, suitable alkylation conditions include a temperature of from about 0° C. to about 500° C., a pressure of from about 20 kPa to about 25000 kPa (0.2 to 250 atmospheres), a feed weight hourly space velocity (WHSV) of from about 0.1 hr$^{-1}$ to about 500 hr$^{-1}$ and an aromatic compound to olefinic hydrocarbon mixture mole ratio of from about 1:1 to about 20:1. The WHSV is based upon the weight of the catalyst composition employed, i.e., the total weight of active catalyst (and binder if present). Typical reaction conditions include a temperature within the range of from about 100° C. to about 350° C., a pressure of from about 100 kPa to about 2500 kPa (1 to 25 atmospheres), a WHSV of from about 0.5 hr$^{-1}$ to about 100 hr$^{-1}$ and an aromatic compound to olefinic hydrocarbon mixture mole ratio of from about 4:1 to about 15:1. Again, the reactants can be in either the vapor phase or the liquid phase and can be neat, i.e., free from intentional admixture or dilution with other material, or they can be brought into contact with the zeolite catalyst composition with the aid of carrier gases or diluents such as, for example, hydrogen or nitrogen.

The alkylation process of the invention produces an alkylaromatic hydrocarbon mixture in which the alkyl side chains are lightly branched and in which most of the aromatic species are located at the 2- or 3-position in the alkyl side chain. The alkylaromatic hydrocarbon mixture is therefore particularly useful as an intermediate in the production of alkylarylsulfonates, which are useful as detergents or surfactants. Processes for sulfonating alkylbenzenes are described in the U.S. Pat. No. 4,298,547, the entire contents of which are incorporated herein by reference. More particularly, alkylaromatic hydrocarbons may be converted to alkylarylsulfonates by sulfonation of the aromatic ring with sulfuric acid. The sulfonation reaction is well known in the art and is commonly carried out by contacting the organic compound with sulfuric acid at temperatures of from about −70° C. to about +60° C. Detailed descriptions of specific commercial processes abound in the literature. See, for instance, pages 60–62 of INDUSTRIAL CHEMICALS, Third Edition, by W. L. Faith et al, published by John Wiley & Sons, Inc.

The invention claimed is:

1. A process for producing a long chain alcohol mixture comprising contacting at least part of the olefinic hydrocarbon mixture produced by preparing an olefinic hydrocarbon mixture comprising at least 5% by weight of mono-olefin oligomers of the empirical formula;

$$C_nH_{2n}$$

where n is greater than or equal to 6, said mono-olefin oligomers comprising at least 20 percent by weight of olefins having at least 12 carbon atoms, said olefins having at least 12 carbon atoms having an average of from about 0.8 to about 2.0 $C_1$–$C_3$ alkyl branches per carbon chain, wherein at least 50% of the branches in the olefins having at least 12 carbon atoms comprising methyl and ethyl branches located at the odd-numbered position in the carbon chain, said process for preparing an olefinic hydrocarbon mixture comprising contacting a feedstock comprising n-butene and propylene in a molar ratio of about 1:0.01 to about 1:0.49 under oligomerization conditions with surface deactivated ZSM-23, wherein said ZSM-23 has been surface deactivated with a sterically hindered nitrogenous base, with carbon monoxide and hydrogen under hydroformylation conditions and in the presence of a hydroformylation catalyst.

2. A process for producing an alkylaromatic compound comprising contacting an aromatic compound with at least part of the olefinic hydrocarbon mixture produced by preparing an olefinic hydrocarbon mixture comprising at least 5% by weight of mono-olefin oligomers of the empirical formula:

$$C_nH_{2n}$$

wherein n is greater than or equal to 6, said mono-olefin oligomers comprising at least 20 percent by weight of olefins having at least 12 carbon atoms, said olefins having at least 12 carbon atoms having an average of from about 0.8 to about 2.0 $C_1$–$C_3$ alkyl branches per carbon chain, wherein at least 50% of the branches in the olefins having at least 12 carbon atoms comprising methyl and ethyl branches located at the odd-numbered positions in the carbon chain, said process for preparing an olefinic hydrocarbon mixture comprising contacting a feedstock comprising n-butene and propylene in a molar ratio of about 1:0.01 to about 1:0.49 under oligomerization conditions with surface deactivated ZSM-23, wherein said ZSM-23 has been surface deactivated with a sterically hindered nitrogenous base, wherein said contacting with said olefinic compound occurs under alkylation conditions and in the presence of an alkylation catalyst.

3. A process for preparing an alkylaryl sulfonate by sulfonating the alkylaromatic compound produced by the process of claim 2.

* * * * *